United States Patent
Brown et al.

(10) Patent No.: US 6,482,449 B2
(45) Date of Patent: Nov. 19, 2002

(54) ENZYMATIC IMPROVEMENT OF PASTA PROCESSING

(75) Inventors: Peter Harris Brown, Glenview, IL (US); John Westcott Finley, Hawthorn Woods, IL (US)

(73) Assignee: Kraft Foods Holdings, Inc., Northfield, IL (US)

( * ) Notice: Subject to any disclaimer, the term of this patent is extended or adjusted under 35 U.S.C. 154(b) by 0 days.

(21) Appl. No.: 09/770,800

(22) Filed: Jan. 26, 2001

(65) Prior Publication Data

US 2002/0102328 A1 Aug. 1, 2002

(51) Int. Cl.⁷ ................................................. A21D 2/00
(52) U.S. Cl. ........................ 426/20; 426/112; 426/128; 426/557; 425/87
(58) Field of Search .............................. 426/112, 115, 426/128, 557, 20; 425/87

(56) References Cited

U.S. PATENT DOCUMENTS

| | | | |
|---|---|---|---|
| 396,567 A | 1/1889 | Held | |
| 2,055,868 A | * 9/1936 | Larsen | 425/87 |
| 2,634,692 A | * 4/1953 | Sherbondy | 425/87 |
| 2,928,533 A | 3/1960 | Loucony | 206/16 |
| 4,360,332 A | 11/1982 | Cyin | 425/191 |
| 4,406,603 A | 9/1983 | Williams | 425/191 |
| 4,731,006 A | 3/1988 | Freda et al. | 425/190 |
| 4,966,537 A | * 10/1990 | Bowles et al. | 425/87 |
| 5,000,355 A | 3/1991 | Pritchard | 222/256 |
| 5,393,217 A | 2/1995 | Cheng | 425/185 |
| 5,409,365 A | 4/1995 | Su et al. | 425/204 |
| 5,427,528 A | 6/1995 | Anderson et al. | 434/83 |
| 5,460,506 A | 10/1995 | Price, IV et al. | 425/190 |
| 5,800,854 A | * 9/1998 | Jaeger | 426/516 |
| RE36,147 E | 3/1999 | Backus et al. | 425/209 |
| 6,039,982 A | 3/2000 | Wagner et al. | 426/18 |
| 6,039,983 A | 3/2000 | Wagner et al. | 426/18 |
| 6,267,999 B1 | * 7/2001 | Romer et al. | 426/115 |
| 6,306,445 B1 | * 10/2001 | Xu et al. | 426/20 |

OTHER PUBLICATIONS

The Good Cook Pasta, 1980, pp. 16–17.*

* cited by examiner

*Primary Examiner*—Lien Tran
(74) *Attorney, Agent, or Firm*—Fitch, Even, Tabin & Flannery

(57) ABSTRACT

An enzymatically treated pasta dough having superior workability and machinability is provided by is prepared by treating pasta dough with an enzyme system consisting essentially of one or more pentosanase enzymes which are essentially free of both proteolytic and amylase activities. The enzymatically treated pasta dough has significantly reduced viscosity as compared to a similar pasta dough which has not been enzymatically treated by the process of this invention. The reduced viscosity of the pasta dough allows significantly reduced head pressures and/or significantly higher throughputs in commercial pasta extrusion systems. Additionally, the pasta product obtained using the present enzymatically treated pasta dough is less prone to checking during drying, thereby allowing faster drying times, more even drying, and reduced energy consumption without sacrificing product quality in commercial operations. Additionally, the enzymatically treated pasta dough has sufficient workability that it can be used in a hand-held and hand-operated extrusion system which allows a consumer to prepare the actual pasta product in the home kitchen. A kit including such a hand-held and hand-operated extrusion system is also provided.

6 Claims, 3 Drawing Sheets

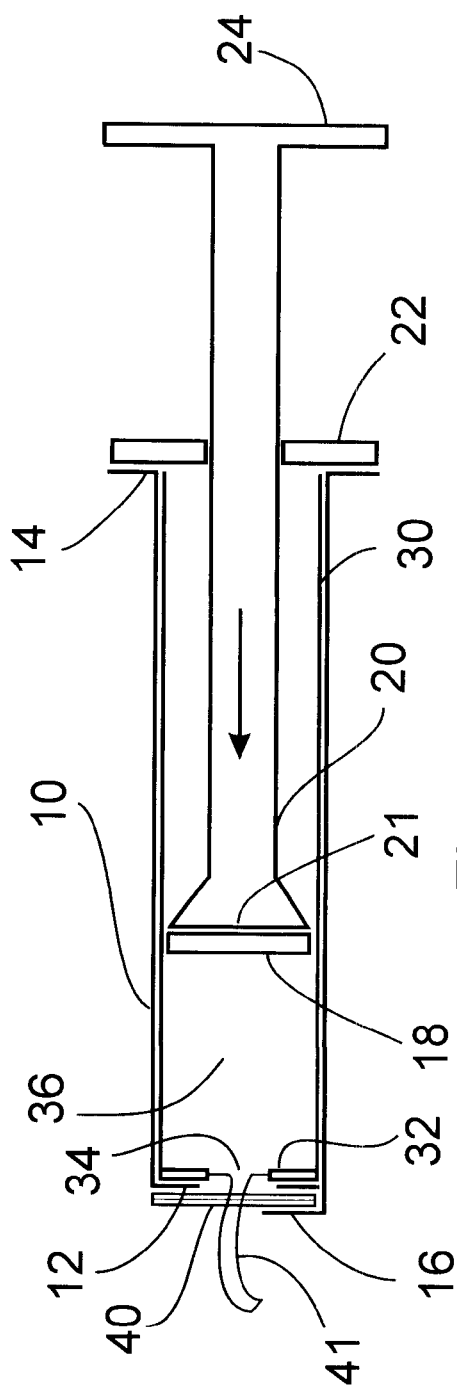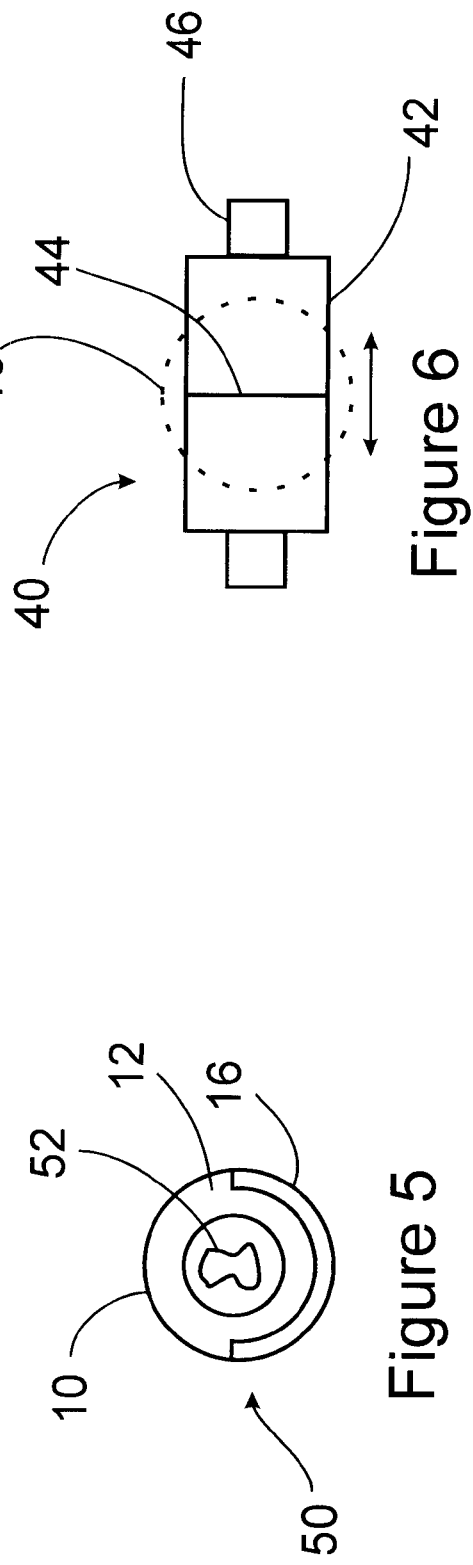

# ENZYMATIC IMPROVEMENT OF PASTA PROCESSING

FIELD OF THE INVENTION

This invention relates to improved pasta dough and an improved method of preparing pasta products. More specifically, this invention provides an improved pasta dough which exhibits less resistance during extrusion, more rapid drying, and reduced checking in the final pasta product. The improved pasta dough is prepared by treating the pasta dough with pentosanase enzymes which are essentially free of both proteolytic and amylase activities. The present invention also provides an improved pasta dough in a kit having a hand-held extrusion system which allows a consumer, including children, to prepare the pasta product in the home kitchen.

BACKGROUND OF THE INVENTION

Pasta is normally prepared by extrusion of a low moisture dough through a die to form the desired shape. Generally, high extrusion head pressures are required due to the high viscosity of the pasta dough. After extrusion, the formed shapes are dried in a process that can take several hours. If not carefully controlled, the pasta can be prone to checking during the drying process.

A number of attempts have been made to provide more workable or machinable dough. For example, U.S. Pat. No. 6,039,983 (Mar. 21, 2000) provides a dough-improving or bread-improving composition containing a pyranose oxidase. The pyranose oxidase is reported to exert an oxidizing effect on dough constituents and to improve the strength of gluten structures in the dough and/or baked products and thereby improve the strength of the dough in addition to the rheological and the handling properties of the dough. Other enzymes, such as cellulase, hemicellulase (e.g., pentosanase or xylanase), lipase, oxidase, peroxidase, protease, peptidase, and amylase. can be used in combination with the primary enzyme (i.e., pyranose oxidase) to improve the dough. Pentosanase is reported as being useful for the partial hydrolysis of pentosans when, in turn, increase the extensibility of the dough. Although this patent is mainly directed to dough useful for preparing bread-type products, it is noted in passing that the pyranose oxidase can be used in the preparation of pasta dough.

U.S. Pat. No. 6,039,982 (Mar. 21, 2000) provides a dough-improving or bread-improving composition containing an L-amino acid oxidase or a benzylamine oxidase to improve gluten strength, stickiness, and rheological properties of the dough as well as the specific volume of the resulting baked goods. The same additional enzymes as in U.S. Pat. No. 6,039,983 can be used in combination with the primary enzymes (i.e., L-amino acid oxidase or benzylamine oxidase). Although this patent is also mainly directed to dough useful for preparing bread-type products, it is again noted in passing that the L-amino acid oxidase or benzylamine oxidase can be used in the preparation of pasta dough.

Nonetheless, extrusion of pasta products still requires high head extrusion pressures due to the high viscosity of the pasta dough and careful drying of the formed pasta to prevent checking. It would be desirable therefore to provide a more workable or machinable pasta dough that would allow a significant reduction in head extrusion pressure in pasta extruders. Moreover, it would be desirable to provide a pasta dough that allows the production of extruded pasta shapes that are less likely to check during drying. The present invention provides such a pasta dough and a method of preparing such a pasta dough. Indeed, it has surprisingly found that the pasta dough of the present invention has such improved workability that it can be used in a hand-held extrusion system which allows a consumer, including children, to prepare the pasta product in the home kitchen.

SUMMARY OF THE INVENTION

The present invention provides an enzymatically treated pasta dough having superior workability and machinability. The enzymatically treated pasta dough has significantly reduced viscosity as compared to a similar pasta dough which has not been enzymatically treated by the process of this invention. The reduced viscosity of the pasta dough allows significantly reduced head pressures and/or significantly higher throughputs in commercial pasta extrusion systems. Additionally, the pasta product obtained using the present enzymatically treated pasta dough is less prone to checking during drying, thereby allowing faster drying times, more even drying, and reduced energy consumption without sacrificing product quality in commercial operations. The textural and organoleptic properties of the cooked pasta prepared using the enzymatically treated pasta dough of this invention is essentially equivalent to a conventional high quality pasta product.

Surprisingly, the enzymatically treated pasta dough of the present invention has sufficient workability that it can be used in a hand-held and hand-operated extrusion system which allows a consumer to prepare the actual pasta product in the home kitchen. Indeed, the enzymatically treated pasta dough can be extruded by a young child using such a hand-held and hand-operated extrusion system. A kit containing such enzymatically treated dough and a hand-held and hand-operated extrusion system is provided. Such a kit allows children to actively participate in meal preparation.

The enzymatically treated dough of this invention is prepared by treating the pasta dough with an enzyme system consisting essentially of one or more pentosanase enzymes which are essentially free of both proteolytic and amylase activities. The enzyme system should not contain enzymes other than such pentosanase enzymes.

BRIEF DESCRIPTION OF THE DRAWING

FIG. 4 illustrates the extrusion system of FIG. 2 in combination with the pasta dough cartridge of FIG. 3.

FIG. 5 illustrates the extrusion die system mounted on extruding or distal end of the extrusion system of FIGS. 2 and 4.

FIG. 6 illustrates a cutting system for use with the extrusion system of FIGS. 2 and 4 for cutting the pasta formed by passage through the die system of FIG. 5.

DETAILED DESCRIPTION OF THE INVENTION

This invention relates to improved pasta dough and an improved method of preparing pasta products. More specifically, this invention provides an improved pasta dough which exhibits less resistance during extrusion, more rapid drying, and reduced checking in the final pasta product. The improved pasta dough is prepared by treating the pasta dough with pentosanase enzymes which are essentially free of both proteolytic and amylase activities. The present invention also provides an improved pasta dough in a kit having a hand-held extrusion system which allows a consumer, including children, to prepare the pasta product in the home kitchen.

High quality, wheat-based flours are preferred in the practice of this invention. The flour should be of the glutenous type and have a minimum average protein content of about 12 to about 13.5 weight percent and preferably a minimum average protein content of about 13 to about 13.5 weight percent. Preferred wheat-based flours comprise 100 percent durum flours, 100 percent semolina flours, blends of about 25 to about 100 parts by weight durum flour and 0 to about 75 parts by weight hard red spring flour, and blends of about 25 to about 100 parts by weight semolina flour and 0 to about 75 parts by weight hard red spring flour. Especially preferred wheat-based flours include 100 percent durum flours, 100 percent semolina flours, blends of about 50 to 100 weight percent durum flour and 0 to about 50 weight percent hard red spring flour, and blends of about 50 to 100 weight percent semolina flour and 0 to about 50 weight percent hard red spring flour, wherein the flour or flour blend has a minimum average protein content between about 13 to about 13.5 weight percent. Generally flours having a granulation size such that about 98 percent minimum pass through a U.S. standard No. 70 sieve (i.e., about 210 micron openings) are acceptable.

Figure 1:
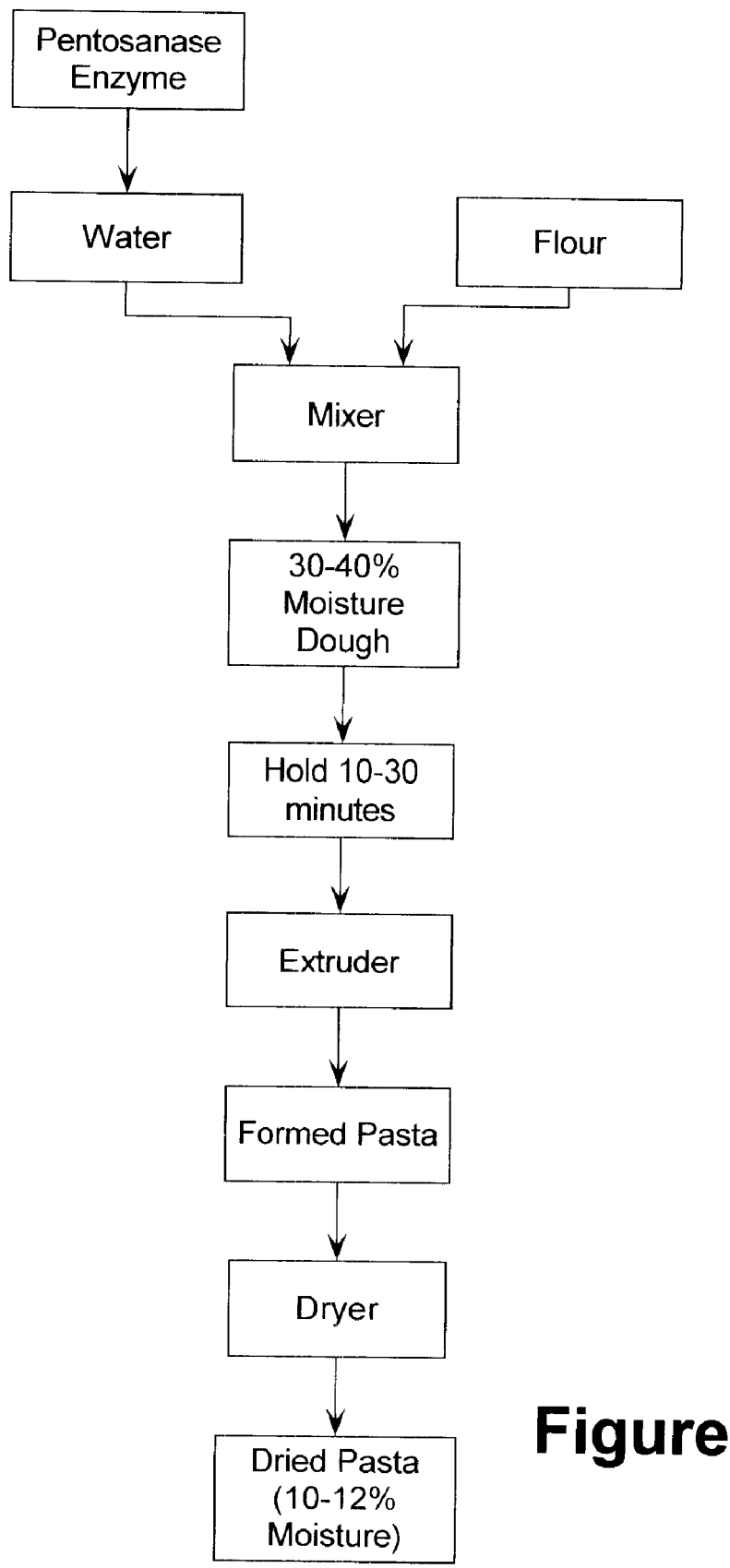
FIG. 1 is a flow diagram illustrating the preparation of the enzymatically treated pasta dough of the present invention and a commercial process for preparing the pasta.

The enzymatically treated dough of this invention is prepared by treating the pasta dough with an enzyme system consisting essentially of one or more pentosanase enzymes which are essentially free of both proteolytic and amylase activities. The enzyme system should not contain enzymes other than such pentosanase enzymes. Specific examples of suitable enzymes include, but not limited to, Bioxylanase 10L and Bioxylanase 10P (Quest International, Hoffman Estates, IL); DEPOL 333P pentosanase, DEPOL 454P endo-xylanase, and DEPOL 453 pentosanase (Biocatalysts, Wales, UK); MultifectXL, GC 140 and GC 260 (Genencor International, Rochester, N.Y.); and Veron MX pentosanase and Veron 191 pentosanase (Rohm Enzyme, Piscataway, N.J.). A preferred process for enzymatically treating pasta dough in a commercial operation is illustrated in FIG. 1. The pentosanase enzyme or enzymes are preferably introduced through the water. The water and flour are then mixed to form a dough. Preferably the water is a temperature of about 10 to about 50° C. during mixing. Generally, the dough contains about 0.001 to about 1.0 percent pentosanase enzyme (equivalent to an enzyme activity of about 45 to about 45,000 enzyme units per pound dough), about 20 to about 75 percent water, and about 25 to about 80 percent flour. More preferably, the dough contains about 0.01 to about 0.5 percent pentosanase enzyme (equivalent to an enzyme activity of about 450 to about 45,000 enzyme units per pound dough), about 25 to about 45 percent water, and about 55 to about 75 percent flour. For purposes of this invention, "enzyme activity" is the amount of enzyme that liberates one micromole of reducing sugar per minute of suitable substrate; enzyme activity can normally be measured using protocols specifically provided by the enzyme manufacturer. The enzymatic treatment is effected by holding the dough at a temperature and for a time sufficient to partially hydrolyze the pentosans present in the flour.

Preferably, the enzyme treatment is sufficient to reduce the viscosity of the pasta dough by at least about 10 percent (relative to a similar pasta dough not enzyme treated); more preferably, the enzyme treatment is sufficient to reduce the viscosity by at least about 25 percent. Generally, a temperature of about 10 to about 60° C. for about 3 to about 60 minutes is sufficient for the partial hydrolysis of the pentosans. More preferably, the enzymatic treatment is at a temperature of about 40 to about 60° C. for about 3 to about 30 minutes.

After sufficient hydrolysis of the pentosans has occurred, the enzyme is preferably inactivated by raising the temperature of the enzymatically treated dough to about 40 to about 110° C. for about 1 to about 20 minutes. More preferably, inactivation is at about 80 to about 110° C. for about 3 to about 10 minutes. Inactivation may occur in a separate process step prior to extrusion or by extrusion at an elevated temperature. Normally, inactivation is preferably carried out by heating the enzymatically treated dough to a temperature of about 80 to about 110° C. for about 3 to about 10 minutes.

The enzymatically treated dough is then extruded using conventional extrusion techniques and equipment to form the desired pasta shapes. Generally, the extrusion is carried out at a temperature of about 15 to about 150° C., and more preferably at a temperature of about 20 to about 50° C. Generally, the pressures required for extrusion for the enzymatically treated pasta dough is at least about 10 percent less as compared to a similar pasta dough which has not been enzymatically treated where essentially the same throughput is obtained. If desired, the enzymatically treated dough can be extruded at a higher pressure to obtain higher capacity (i.e., higher throughput). Suitable shaped pasta includes, for example, elbow macaroni, elbow spaghetti, shells, mafalda, spaghetti, fettuccine, vermicelli, and the like. If desired, other shapes, including, for example, animal shapes, cartoon shapes, sport shapes, superhero character shapes, movie character shapes, and the like, which will especially appeal to children can be used.

The shaped and extruded pasta is then dried using conventional techniques and equipment. Generally, the pasta shapes are dried at a temperature of about 20 to about 60° C. for about 10 to about 15 minutes to obtain a moisture level of about 10 to 12 percent. Generally, the pasta shapes prepared using the enzymatically treated dough of this invention can be dried at a faster rate than conventional pasta without significant checking. Generally, drying rates of at least about 10 percent faster can be used without significant checking. The drying step will complete the enzyme inactivation if it has not already been completed. The dried pasta can then be packaged using conventional techniques.

As noted above, the enzymatically treated pasta dough of this invention has such improved workability that it can be used in a hand-held extrusion system which allows a consumer, including children, to prepare the pasta product in the home kitchen. Thus, the present invention allows for a pasta-making kit suitable for preparing pasta shapes in the home kitchen and then preparing a side dish or a meal using the just formed pasta shapes. The enzymes and the enzyme treatment process used for preparing such dough is essentially the same as that just described above for a commercial pasta manufacturing operation. Preferably, the enzymatically treated dough is then exposed to a temperature of about 40 to about 110° C. for about 1 to about 20 minutes, and more preferably to a temperature of about 80 to about 110° C. for about 3 to about 10 minutes, to inactivate the enzyme and then packaged into a suitable container or cartridge (see, e.g., FIG. 3) for use with pasta-making kit. Alternatively, the enzyme treated dough can be directly packaged in a suitable container or cartridge without enzyme inactivation, thus allowing maximum hydrolysis of the pentosans during dough storage at either room (i.e., about 15 to about 25° C.) or refrigeration (i.e., about 2 to about 15° C.) temperatures; in such a case, enzyme inactivation would occur when the pasta is ultimately cooked (generally at about 80 to about 110° C. for about 3 to 15 minutes) by the consumer. Preferably the container or cartridge is sealed to protect the pasta dough against air and/or moisture until such time as the dough is used. Preferably, the seals are easily removed by hand when it is desired to use the dough.

Figure 2:
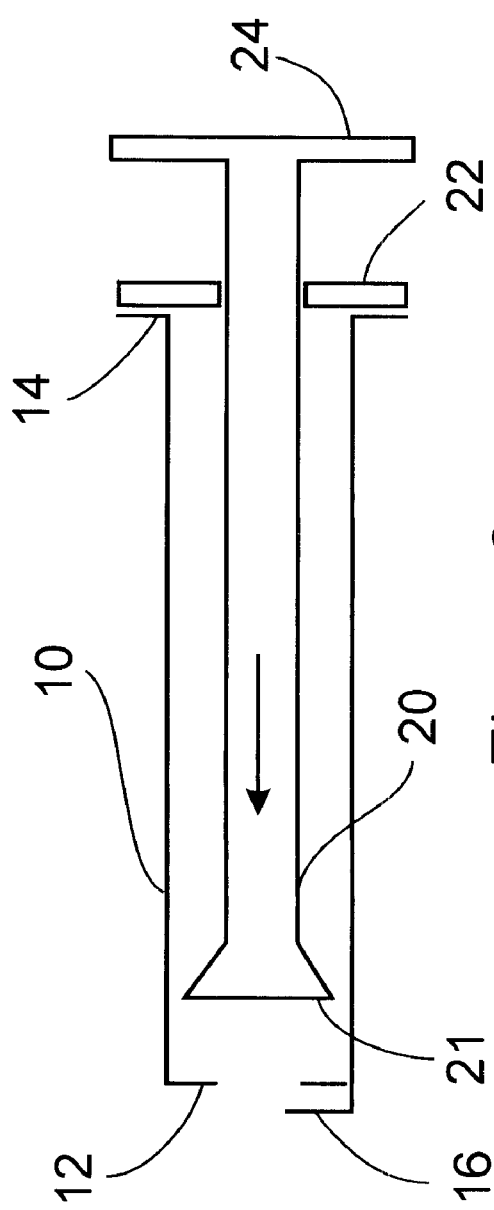
FIG. 2 illustrates a hand-held and hand-operated extrusion system designed for use in the home kitchen using the enzymatically treated pasta dough of the present invention.
Figure 3:
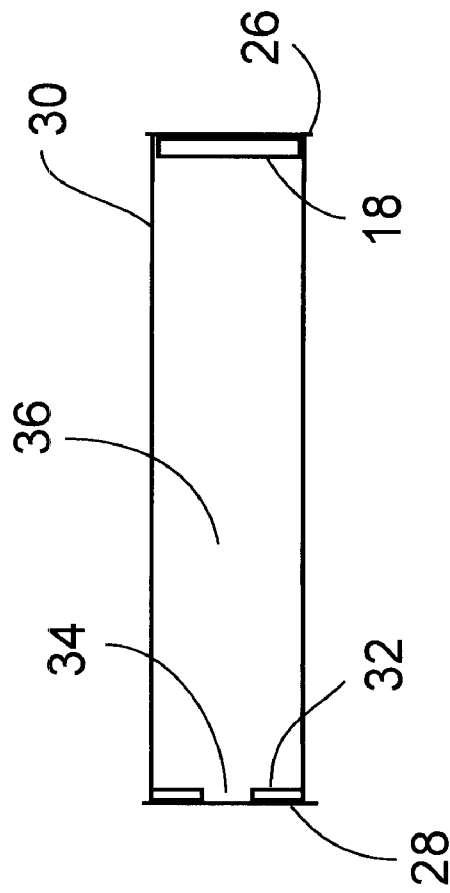
FIG. 3 illustrates a cartridge containing the enzymatically treated pasta dough of the present invention which can be used in the extrusion system of FIG. 2.

A hand-held pasta extruding system suitable for using with the enzymatically treated pasta dough of the present invention is illustrated in FIGS. 2–6. FIG. 2 illustrates a hand-held and hand-operated extrusion system designed for use in the home kitchen using the enzymatically treated pasta dough of the present invention. The extrusion system consists of a extrusion cylinder 10 and a extrusion ram 20. FIG. 3 illustrates a cartridge 30 containing the enzymatically treated pasta dough 36 of the present invention which can be used in the extrusion system of FIG. 2. FIG. 4 illustrates the extrusion system of FIG. 2 in combination with the pasta dough cartridge 30 of FIG. 3. FIG. 5 illustrates the extrusion die system 50 which is mounted on the distal end of extrusion cylinder 10. FIG. 6 illustrates the pasta cutting system 40 which is also mounted on the distal end of extrusion cylinder 10.

As shown in FIG. 2, the extrusion system comprises extrusion cylinder 10 and a extrusion ram or screw 20 which fits inside extrusion cylinder 10 and can move from the proximal end to the distal end of extrusion cylinder 10 as illustrated by the arrow in the figure. Although the extrusion cylinder 10 is preferably cylindrical, elongated tubes having other cross-sectional shapes can also be used if desired. The extrusion ram or screw 20 has a handle 24 at its proximal end and a pressure surface 21 at its distal end and is designed to slide or to be screwed within the extrusion cylinder 10. The extrusion cylinder 10 has ring 12 and a mounting bracket or holder 16 at its distal end and a connector plate 14 at its proximal end. The ring 12 forms the distal end of the extrusion cylinder 10. The connector plate 14 forms the proximal end of the extrusion cylinder 10 and is designed to mate with the removable end cap 22. The removable end cap 22 allows the extrusion ram to be removed so that the extrusion cylinder 10 can be filled with dough when desired.

The pasta dough cartridge 30 containing pasta dough 36 is illustrated in FIG. 3. The pasta dough cartridge 30 is designed to fit within extrusion cylinder 10 (see FIG. 4). The pasta dough cartridge 30 has removable seals 26 and 28 at its proximal and distal ends, respectively; preferably these seals 26 and 28 can be removed by pealing by hand. These removal seals 26 and 28 are preferably air and moisture resistance and allow the pasta dough to be maintained at ambient temperature for extended shelf lives (i.e., generally at least about 24 months). The pasta dough cartridge 30 also has a pressure plate 18 at its proximal end and an end plate 32 with opening 34 at its distal end. The pressure plate is movable within the pasta dough cartridge 30 such that, once removable seals 26 and 28 are removed and when engaged by the pressure surface 21, the pasta dough 36 is forced towards the distal end of the pasta dough cartridge 30 and out through opening 34.

FIG. 4 illustrates the extrusion system containing the pasta dough cartridge 30 in operation. The end plate 32 of the pasta dough cartridge 30 rests against the ring 12 of the extrusion cylinder 10. The extrusion ram or screw 20 is activated by applying hand pressure or screwing action through the handle 24 towards the distal end of the extrusion cylinder 10, thereby allowing the pressure plate 21 to engage pressure plate 18. Movement of the extrusion ram 20 in the direction of the arrow in FIG. 4, forces pasta dough 36 through opening 34 to form the extrudate 41.

Although the pasta dough cartridge 30 preferably contains the pressure plate 18 as illustrated in FIGS. 3 and 4, such a pressure plate 18 is not required. If the pressure plate 18 is eliminated, pressure plate 21 could act directly on the pasta dough 34 to form the extrudate 41. The extrusion die 52 (see FIG. 5) can be mounted on the distal end of extrusion cylinder 10 or included as part of the pasta dough cartridge 30 (i.e., illustrated as opening 34 in FIG. 3). Preferably, both the extrusion die 52 and the pressure plate 18 are included in the pasta dough cartridge 30. In that case, both the extrusion die and the pressure plate 18, which will contact the pasta dough 34 during extrusion, are sealed with the pasta dough 34 until actual use and are, therefore, less likely to be exposed to sources of contamination. Placing the extrusion die 52 within the pasta dough cartridge 30 also allow a better seal with the distal end (ring 12) of the extrusion cylinder 10 during operation and allows better control of the extruding process.

The extrusion die 52 can be modified to form extrudates 41 having various cross sectional shapes. Such shapes can include, but are not limited to, cylinders, ovals, squares, rectangles, stars, animal or other shapes, cartoon characters, letters, numbers, and the like. Such shapes can be designed to appeal to children.

Cutter assembly 40 is designed to be mounted on the distal end of extrusion cylinder 10 via mounting bracket 16 to cut the extrudate 41 to the appropriate length; in FIG. 6, the distal end of extrusion cylinder 10 is shown as a dashed line to illustrate the orientation of the cutter assembly 40 to the extruder system. Cutter assembly 40 consists of bracket 42 having a cutting wire or other device 44 along with handles 46 at either end. In operation, the cutter assembly 40 is moved by hand back and forth as indicated by the arrow such that cutting wire 44 cuts the extrudate 41 to the appropriate length. Preferably, the cutting wire or other device 44 allows the extrudate 41 to be cut as desired but does not have sharp exposed surfaces and can, therefore, be used by children. Of course, as with any cooking experience in the kitchen, the appropriate level of adult supervision, largely depending on the age and experience of the child, should be maintained. In operation, the extrusion ram 20 is used to force extrudate 41 through the extrusion die 52 at which point the cutter assembly 40 is used to cut the extrudate 41 to the desired length. Once the pasta is formed using the extrusion system, the pasta can be cooked and combined with the appropriate sauce using conventional techniques. Preferably, the extrusion system, one or more pasta dough cartridges 30, and a dry mix for preparing the pasta sauce is combined in kit form. The extrusion system can be fabricated for single (i.e., disposable) or multiple use. If a multiple use extrusion system is desired, the extrusion system and the pasta dough cartridges (preferably with the sauce mix or components) can be sold in separate kits.

The enzymatically treated pasta dough of the present invention allows the use of such a hand-held and hand-operated extrusion system. Indeed, the enzymatically treated pasta dough of this invention has sufficient workability so that the pasta can be made by children. Conventional pasta dough does not have sufficient workability to be used in such an extrusion system.

We claim:

1. A kit for preparing pasta by hand, said kit comprising (1) a hand-held and hand-operated extrusion system comprising an extrusion cylinder and an extrusion ram or screw and (2) a sealed container to fit within the extrusion cylinder containing a pasta dough;

wherein the sealed container can be unsealed when ready to use, placed in the extrusion cylinder, and pasta dough extruded using the extrusion ram or screw to form the pasta, wherein the pasta dough comprises dough treated with an enzyme system consisting essentially of one or more pentosanase enzymes which are essentially free of both proteolytic and amylase activities, wherein the treatment with the one or more pentosanase enzymes is sufficient to partially hydrolyze pentosanase present in the dough and to provide a pasta dough with improved workability and reduced viscosity, and wherein the pasta which results from the use of the kit dries more quickly and with reduced checking than conventional pasta.

2. The kit of claim 1 wherein the pasta dough is prepared by a method comprising (1) preparing a dough comprising about to 55 about 75 percent flour, about 0.01 to about 0.5 percent of an enzyme system consisting essentially of the one or more pentosanase enzymes, and about 25 to about 45 percent water; and (2) enzymatically treating the dough at about 40 to about 60° C. for about 3 to about 30 minutes to partially hydrolyze pentosans present in the dough and to provide the pasta dough with improved workability and reduced viscosity.

3. The kit of claim 2, wherein the enzymatic treatment of the dough is sufficient to reduce the dough viscosity by at least about 25 percent.

4. The kit of claim 1 further comprising an extrusion die and a cutting assembly whereby the pasta dough can be extruded through the extrusion die and then cut into appropriate lengths with the cutting assembly to form the pasta.

5. The kit of claim 2 further comprising an extrusion die and a cutting assembly whereby the pasta dough can be extruded through the extrusion die and then cut into appropriate lengths with the cutting assembly to form the pasta.

6. The kit of claim 3 further comprising an extrusion die and a cutting assembly whereby the pasta dough can be extruded through the extrusion die and then cut into appropriate lengths with the cutting assembly to form the pasta.

* * * * *